US00PP12790P2

(12) United States Plant Patent
Trees

(10) Patent No.: US PP12,790 P2
(45) Date of Patent: Jul. 23, 2002

(54) VERBENA PLANT NAMED 'BALAZPLUM'

(75) Inventor: Scott Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/822,610

(22) Filed: Mar. 30, 2001

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Kent L. Bell
(74) *Attorney, Agent, or Firm*—Gardner Carton & Douglas

(57) ABSTRACT

A new and distinct Verbena plant named 'Balazplum', characterized by its purple flowers, mounded trailing habit, and deeply cleft, dark green leaves.

2 Drawing Sheets

LATIN NAME OF GENUS AND SPECIES OF PLANT CLAIMED

*Verbena hybrida.*

VARIETY DENOMINATION

'Balazplum'.

BACKGROUND OF INVENTION

The present invention comprises a new and distinct verbena plant, botanically known as *Verbena hybrida*, and hereinafter referred to by the cultivar name 'Balazplum'.

The new cultivar was developed by the inventor through a controlled breeding program during 1998 at Arroyo Grande, Calif. The objective of the breeding program was the development of verbena cultivars with semi-trailing mounded habit, continuous flowering, excellent basal branching and small, dark green foliage.

The female (seed) parent of 'Balazplum' was the proprietary verbena cultivar designated PAS36117 (not patented), which exhibits a semi-trailing habit, dark purple flowers and serrated, medium green foliage. The male (pollen) parent of 'Balazplum' was the commercially available verbena cultivar, 'Temari Patio Hot Pink' (not patented), which exhibits a vigorous, trailing habit, hot pink flowers and dark green foliage.

Asexual reproduction of the new cultivar by terminal cuttings in Arroyo Grande, Calif. and West Chicago, Ill. has demonstrated that the characteristics of the new cultivar as herein described are firmly fixed and retained through successive generations of such asexual propagation.

SUMMARY OF INVENTION

It was found that the cultivar of the present invention:

(a) exhibits purple flowers, (b) forms deeply cleft, dark green foliage (c) exhibits a good basal branching character and (d) exhibits a mounded and trailing growth habit.

The new cultivar of the present invention can be compared to 'Temari Bright Pink'. In side by side comparison, plants of the new cultivar differ from plants of 'Temari Bright Pink' by the following characteristics: it is found that the new cultivar is taller, has larger more deeply cleft leaves and flowers and calyx of a different color as detailed in TABLE A.

When the new cultivar of the present invention is compared to its seed parent, PAS36117, the new cultivar is distinguished from 'PAS36117' primarily in petal coloration and leaf margin. When the new cultivar of the present invention is compared to its pollen parent, 'Temari Patio Hot Pink', the new cultivar is distinguished from 'Temari Patio Hot Pink' primarily in petal coloration.

BRIEF DESCRIPTION OF THE PHOTOGRAPH

The accompanying photographs illustrate the overall appearance of the new cultivar as true as it is reasonably possible to obtain colored reproductions of this type. Color in the photographs may differ slightly from the color values cited in the detailed botanical description which accurately describe the actual colors of the new Verbena.

Sheet 1 depicts the trailing habit of 'Balazplum'.

Sheet 2 depicts a side perspective view of 'Balazplum'. The plants were grown in a greenhouse at West Chicago, Ill., U.S.A.

DETAILED BOTANICAL DESCRIPTION

The 'Balazplum' cultivar has not been observed under all possible environmental conditions to date. Accordingly, it is possible that the phenotype may vary somewhat with variations in the environment, such as temperature, light intensity, and day length.

The chart used in the identification of colors described herein is the R.H.S. Colour Chart of The Royal Horticultural Society, London, England. The color values were deter mined on Aug. 15, 2000. The readings were taken between 1:00 and 3:00 p.m. under natural daylight conditions. The plants used for the descriptions were produced from cuttings taken from stock plants and were grown for about 11 weeks after planting rooted cuttings in 10 cm pots in a double poly carbonate covered greenhouse in West Chicago, Ill. under conditions comparable to those used in commercial practice while utilizing a soilless growth medium and maintaining temperatures of approximately 72° F. during the day and approximately 65° F. during the night.

Classification:

*Botanical.*—*Verbena hybrida* cultivar 'Balazplum'.

Parentage:

*Female parent.*—Proprietary seedling designated PAS36117.

*Male parent.*—'Temari Patio Hot Pink'.

Propagation:

*Type cutting.*—Terminal tip.

*Time to initiate roots.*—Approximately 14–21 days with the shorter times generally being experienced in the summer and the longer times in the winter.

*Root description.*—Fibrous, branching.

Plant description:

*Habit of growth.*—Moderately vigorous with good basal branching. Pinching improves basal branching. A mature plant, 8 to 10 weeks after the planting of a rooted cutting, commonly measures approximately 28.8 cm in height and approximately 38.3 cm in width.

*Form.*—Upright mounded and trailing.

*Stem.*—Tetragonal, 2 mm in diameter, with moderate pubescence, 146C with reddish anthocyanin coloration along all four edges. Internode length is approximately 1.1 cm.

*Foliage.*—Leaves are opposite, ovate with deeply cleft margin, acute apex, attenuate base, and densely covered with short stiff hairs on upper and lower surface, especially along veins on lower surface. Approximately 2 cm in length and approximately 1.2 cm at widest point. Upper surface of mature leaf is 137A, lower surface is 137C, venation of upper and lower surface is 146D. Petiole length is approximately 2 mm; color is 146D.

Flowering description:

*Flowering habit.*—Freely flowering.

*Natural flowering season.*—Year round in greenhouse environment. April through October in garden.

*Inflorescence type.*—Corymb. Approximately 3 cm deep and 4 cm in diameter with approximately 21 fully opened flowers per inflorescence at any one time.

*Peduncle.*—Approximately 4.3 cm in length, 1 mm in diameter, 146C.

*Bud.*—Round to oval, approximately 4 mm in diameter, 89A.

*Petals.*—Five, fused at base, somewhat overlapping.

*Flower diameter.*—Approximately 1.6 cm. Corolla tube approximately 1.3 cm long.

*Calyx.*—Approximately 1.2 cm in length, 1 mm in diameter, 5 toothed, 5 ribbed, with stipules, 146C (both surfaces) with small area of reddish anthocyanin coloration at one point along one rib.

*Flower color.*—Fully opened, upper surface: redder than 83A, bluer and much darker than 80A; lower surface: 83B at apex, gradually changing to 84C at base. Whiskers of closest to 83D surround the opening of the corolla tube.

*Reproductive organs.*—There are 4 stamens and one pistil.

Seed production: Seed production has not been observed.

Disease resistance: Resistance to pathogens has not been observed.

TABLE A

| CHARACTERISTIC | 'BALAZPLUM' | 'TEMARI BRIGHT PINK' |
|---|---|---|
| PLANT HEIGHT | 28.8 CM | 23.8 CM |
| INTERNODE LENGTH | 1.1 CM | 1.4 CM |
| LEAF LENGTH × LEAF WIDTH | 2 × 1.2 CM | 2.9 '3 1.8 CM |
| CALYX COLOR | 146C WITH REDDISH ANTHOCYANIN COLORATION ALONG ONE RIB AND TOP MARGIN | 146C WITH ANTHOCYANIN COLORATION AT TOP MARGIN |
| FLOWER COLOR-UPPER SURFACE-RHS | REDDER THAN 83A AND BLUER AND MUCH DARKER THAN 80A | 57B |
| FLOWER COLOR-LOWER SURFACE-RHS | 83B AT MARGIN; GRADUALLY FADES TO 84C AT BASE | 57C AT MARGIN; GRADUALLY FADES TO 62B AT BASE |

I claim:

1. A new and distinct cultivar of *Verbena hybrida* plant named Balazplum substantially as herein shown and described, which:

(a) exhibits purple flowers, (b) forms deeply cleft, dark green foliage, (d) exhibits a good basal branching character and (e) exhibits a upright mounded growth habit.

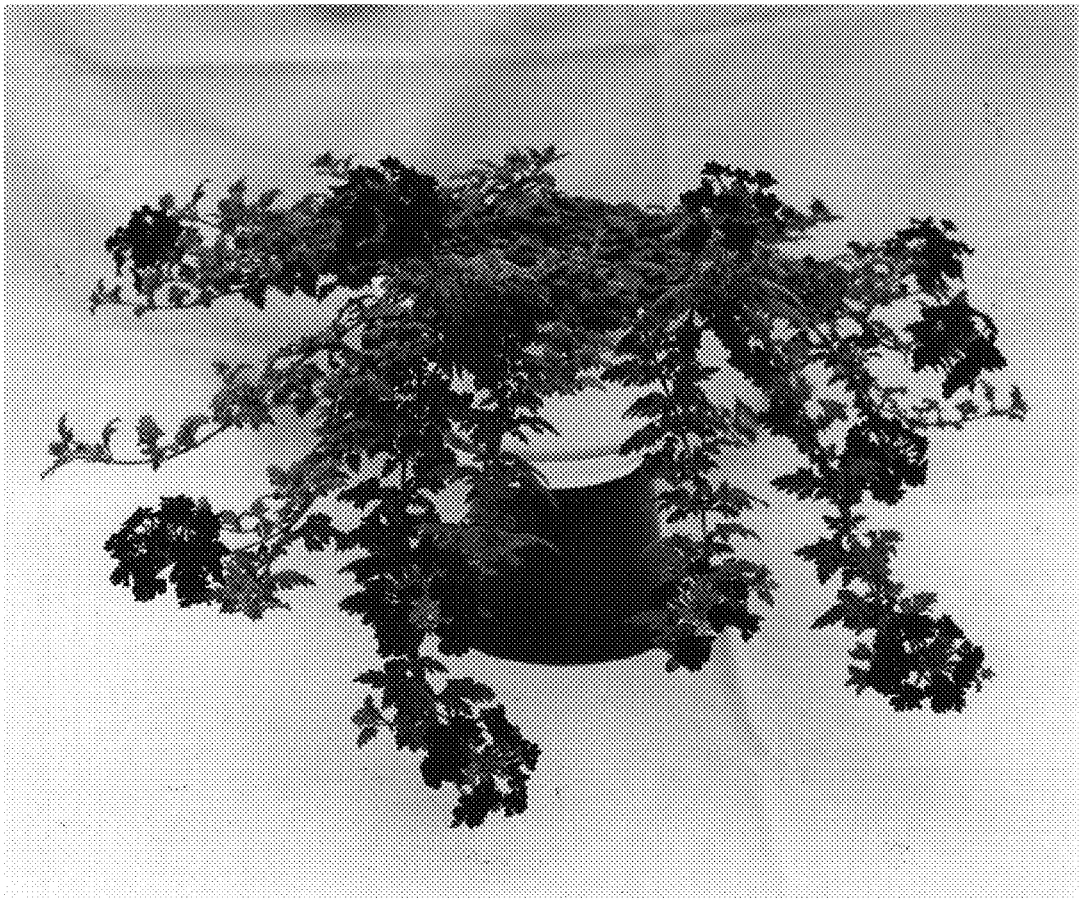

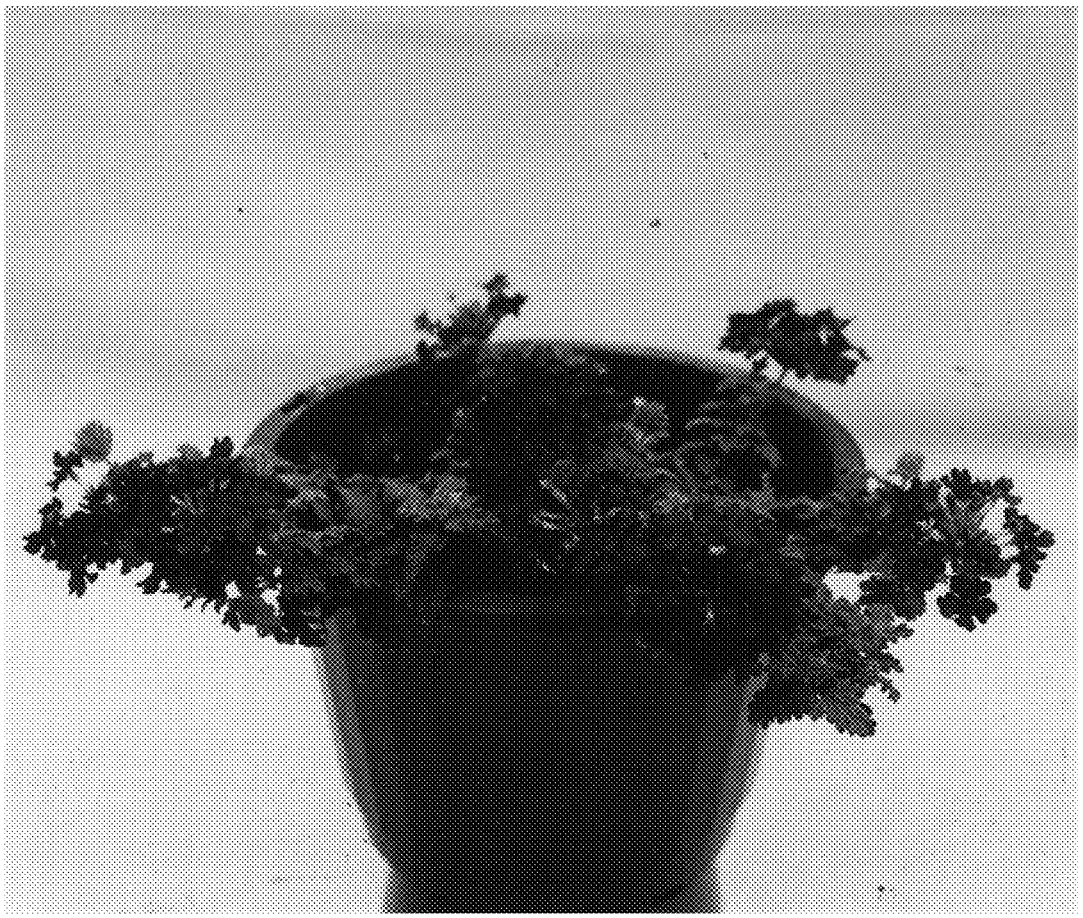

* * * * *